US011096897B2

(12) United States Patent
Sagalowicz et al.

(10) Patent No.: US 11,096,897 B2
(45) Date of Patent: Aug. 24, 2021

(54) CONTROLLED RELEASE OF CAFFEINE

(71) Applicant: NESTEC S.A., Vevey (CH)

(72) Inventors: Laurent Sagalowicz, Blonay (CH); Raffaele Mezzenga, Volkestwil (CH); Renata Negrini, Zurich (CH); Isabelle Martiel, Zurich (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/535,836

(22) PCT Filed: Dec. 3, 2015

(86) PCT No.: PCT/EP2015/078591
§ 371 (c)(1),
(2) Date: Jun. 14, 2017

(87) PCT Pub. No.: WO2016/096468
PCT Pub. Date: Jun. 23, 2016

(65) Prior Publication Data
US 2017/0367984 A1 Dec. 28, 2017

(30) Foreign Application Priority Data
Dec. 15, 2014 (EP) .................................. 14198056

(51) Int. Cl.
A61K 9/48 (2006.01)
A61K 36/53 (2006.01)
A61K 31/685 (2006.01)
A61K 9/00 (2006.01)
A23K 20/158 (2016.01)
A23L 33/115 (2016.01)
A23L 33/105 (2016.01)
A23K 20/116 (2016.01)
A61K 36/752 (2006.01)
A61K 31/522 (2006.01)
A23K 50/40 (2016.01)

(52) U.S. Cl.
CPC .......... A61K 9/4875 (2013.01); A23K 20/116 (2016.05); A23K 20/158 (2016.05); A23K 50/40 (2016.05); A23L 33/105 (2016.08); A23L 33/115 (2016.08); A61K 9/0056 (2013.01); A61K 31/522 (2013.01); A61K 31/685 (2013.01); A61K 36/53 (2013.01); A61K 36/752 (2013.01)

(58) Field of Classification Search
None
See application file for complete search history.

(56) References Cited

U.S. PATENT DOCUMENTS 6,475,530 B1 11/2002 Kuhrts
8,158,687 B2 * 4/2012 Yaghmur ............... A23D 7/011
426/89
8,388,985 B2 * 3/2013 Leser ................... A23D 7/0053
424/400
8,920,862 B2 * 12/2014 Sagalowicz .......... A23D 7/0053
426/533
2003/0064104 A1 4/2003 Stillman
2004/0156816 A1 8/2004 Anderson
2007/0213234 A1 * 9/2007 Yaghmur ............. A23D 7/0053
508/110
2008/0171085 A1 7/2008 Elnekave et al.
2008/0255247 A1 * 10/2008 Sagalowicz ............... A61K 8/06
514/772
2010/0009039 A1 * 1/2010 Robinson ............... A23C 9/142
426/72

FOREIGN PATENT DOCUMENTS

| CN | 1503633 A | 4/2007 |
| CN | 1953735 A | 4/2007 |
| EP | 1504671 | 2/2005 |
| JP | 2004147578 A | 5/2004 |
| JP | 2010195761 A | 9/2010 |
| JP | 2013014644 A | 1/2013 |
| WO | 9511595 A1 | 5/1995 |
| WO | 2014151109 A1 | 9/2014 |

OTHER PUBLICATIONS

European Commission, Scientific committee on Food "Opinion of the Scientific Committee on Food on eucalyptol" https://ec.europa.eu/food/sites/food/files/safety/docs/sci-com_scf_out126_en.pdf, p. 1-10, 2002.*
Martiel et al. "Phospholipid-based nonlamellar mesophases for delivery systems: Bridging the gap between empirical and rational design" Advances in Colloid and Interface Science, 2014, vol. 209, pp. 127-143.
Vallooran et al. "Controlling Anisotropic Drug Diffusion in Lipid Fe3O4 Nanoparticle Hybrid Mesophases by Magnetic Alignment" Langmuir, 2013, vol. 29, pp. 999-1004.
Hiwale et al., "Liquid-Crystal Based Formulations for Topical Drug Delivery", Journal of Dispersion Science and Technology, vol. 34, Issue No. 9, Sep. 2, 2013, pp. 1286-1293, XP055169863.
Shah et al., "Cubic phase gels as drug delivery systems", Advanced Drug Delivery Reviews, Elsevier, Amsterdam, vol. 47, Issue No. 2-3, Apr. 25, 2001, pp. 229-250, XP002320651.
Liang et al., "Comprehensive Utilization of Tea Resources", Zhejiang University Press, 1st edition, Nov. 2013, pp. 119-120.

(Continued)

Primary Examiner — Erin E Hirt
(74) Attorney, Agent, or Firm — K&L Gates LLP

(57) ABSTRACT

The present invention relates to an edible composition having a lipid continuous phase and self-assembled structures, the composition comprising oil, phospholipids, caffeine and water. Further aspects of the invention are the use of a composition to provide controlled release of caffeine, a composition for use in the treatment or prevention of drowsiness, the non-therapeutic use of a composition to increase mental alertness, and an edible capsule.

17 Claims, 6 Drawing Sheets

(56) References Cited

OTHER PUBLICATIONS

Office Action Received for Application No. 201580065656.4, dated Apr. 2, 2020,17 pages(05 pages of English translation and 12 pages of official copy).
Dulloo et al., Normal Caffeine Consumption: Influence on Thermogenesis and Daily Energy Expenditure in Lean and Postobese Human Volunteers 1-4, American Journal of Clinical Nutrition, vol. 49, 1989, pp. 44-50.
Chinese Office Action for Appl No. P2017-531594 dated May 12, 2020.

\* cited by examiner

CONTROLLED RELEASE OF CAFFEINE

CROSS REFERENCE TO RELATED APPLICATIONS

The present application is a National Stage of International Application No. PCT/EP2015/078591, filed on Dec. 3, 2015, which claims priority to European Patent Application No. 14198056.5, filed on Dec. 15, 2014, the entire contents of which are being incorporated herein by reference.

FIELD OF THE INVENTION

The present invention relates to an edible composition having a lipid continuous phase and self-assembled structures, the composition comprising oil, phospholipids, caffeine and water. Further aspects of the invention are the use of a composition to provide controlled release of caffeine, a composition for use in the treatment or prevention of drowsiness, the non-therapeutic use of a composition to increase mental alertness, and an edible capsule.

BACKGROUND OF THE INVENTION

It is well known that various stimulants can be administered to people to impart alertness and/or combat sleepiness. A typical stimulant used for these purposes is caffeine. Conveniently, caffeine is found in beverages such as coffee, tea and some carbonated soft drinks. One of the most common forms of administering caffeine is by consuming a cup of hot coffee early in the morning to help the individual to become more alert when beginning the day.

Ingesting large amounts of coffee or other caffeinated beverages is disadvantageous from the standpoint that the beverages must be continually consumed to provide the desired caffeine level in the individual's system and so achieve an appropriate level of alertness. It may not be convenient or desired to drink a series of cups of coffee during the day. What is needed therefore is a product for easily administering caffeine so that the required level of caffeine and hence the desired level of alertness is sustained over a long period.

Providing sustained release of caffeine presents particular challenges as caffeine is an unusual molecule which can easily cross lipid membranes such as the ones present in self-assembled structures. Caffeine is known to passively cross biological membranes [A. McCall, W. Millington, R. Wurtman, Blood—brain barrier transport of caffeine: dose-related restriction of adenine transport, Life Sci. 31 (24) (1982) 2709-2715; M. Paloncýová, K. Berka, M. Otyepka, Molecular insight into affinities of drugs and their metabolites to lipid bilayers, J. Phys. Chem. B 117 (8) (2013) 2403-2410.]. Its permeation coefficient through PC bilayers is about 2·10-5 cm/s [T. Nisisako, Sa Portonovo, J. J. Schmidt, Microfluidic passive permeability assay using nanoliter droplet interface lipid bilayers, Analyst 138 (22) (2013) 6793-6800.]. A sustained release system which works for a hydrophilic molecule such as glucose would not necessarily be effective for caffeine.

Sustained release caffeine compositions are generally known, for example EP0716853 describes a composition comprising micro-particles including a biodegradable matrix of at least one water-soluble material and caffeine, the caffeine being in the form of solid particles which are distributed throughout the matrix. A water insoluble material such as shellac may be coated onto the micro-particles to delay the release of the caffeine.

WO2007060177 describes an oil-in-water emulsion in which the dispersed oil droplets exhibit a self-assembled structure. The emulsion may contain an active element such as caffeine.

However, there remains a need to provide a wider range of sustained release caffeine compositions; for example compositions which do not require the production of complex solid structures such as coated micro-particles, or compositions which do not require the formation and maintenance of stable oil-in-water emulsion systems. It would furthermore be advantageous to be able to provide sustained release caffeine compositions comprising natural ingredients.

An object of the present invention is to improve the state of the art and to provide an alternative composition to overcome at least some of the inconveniences described above. Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to". The object of the present invention is achieved by the subject matter of the independent claims. The dependent claims further develop the idea of the present invention.

SUMMARY OF THE INVENTION

The present invention provides in a first aspect an edible composition having a lipid continuous phase which is liquid at 25° C. and self-assembled structures; the composition comprising oil, phospholipids, caffeine and water. In an aspect of the invention the edible composition is for use in the treatment or prevention of drowsiness.

In a second aspect, the invention relates to a non-therapeutic use of the edible composition to increase mental alertness. In a third aspect the invention relates to the use of the composition to provide a controlled release of caffeine. In a further aspect, the invention provides an edible capsule containing the composition.

It has been surprisingly found by the inventors that a caffeine-containing composition having a lipid continuous phase and self-assembled structures provides a controlled release of caffeine. For example, a system containing limonene, phospholipids, caffeine and water having cubic micellar self-assembled structures, was found to have a diffusion coefficient 20 times lower than for caffeine in water. This provides a sustained release of caffeine. The self-assembled structures in the composition of the invention delineate very small aqueous domains which have diameters in the submicrometer range. Without wishing to be bound by theory, the inventors believe that the water-soluble caffeine molecules, originally situated in the aqueous domains, have to diffuse a greater distance through the lipid domain than the aqueous domain in order to diffuse out of the composition. As the diffusion rate is very much slower in lipid than in water this results in a slow, controlled release of caffeine. The diffusion rate obtained is slower than in a water-in-oil emulsion as the aqueous domains are smaller and therefore the distance to travel in the lipid domain is higher.

DETAILED DESCRIPTION OF THE INVENTION

Figure 1:
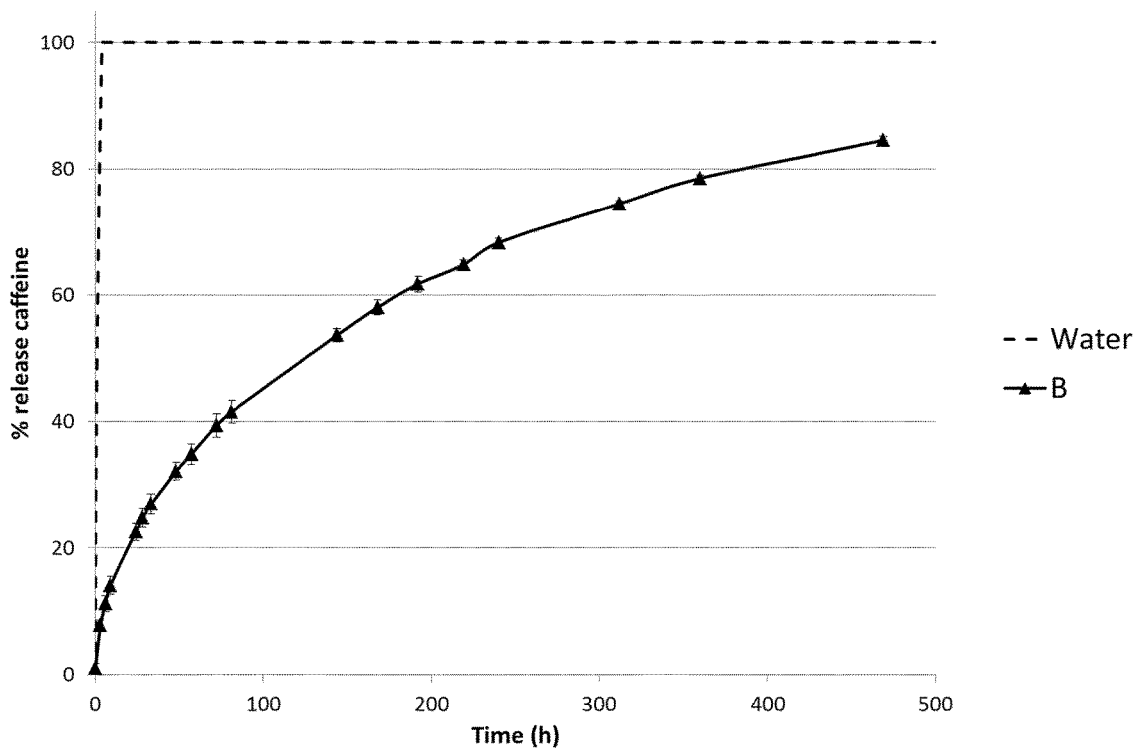
FIG. 1 shows the release of caffeine as function of time for a limonene/phospholipid composition having reversed micellar cubic structure (B) compared to caffeine release from water.

Consequently the present invention relates in part to an edible composition having a lipid continuous phase which is liquid at 25° C. and self-assembled structures; the composition comprising oil, phospholipids, caffeine and water. The term "edible" refers to substances which can be eaten safely. Whilst the current invention is not limited to substances permitted for consumption in any particular jurisdiction, edible compositions may for example comprise materials approved for human consumption by the U.S. Food and Drug Administration. The term 'self-assembled' refers to the spontaneous formation of associates or sub-micrometer structures by separate molecules. Molecules in self-assembled structures find their appropriate location based solely on their structural and chemical properties due to given intermolecular forces, such as hydrophobic, hydration, phase segregation or electrostatic forces [Evans, D. F.; Wennerström, H. (Eds.); 'The Colloidal Domain', Wiley-VCH, New York, (1999)]. The result of self-assembly does not depend on the process of preparation itself and corresponds to a state of minimum energy (stable equilibrium) of the system. They are very different from oil in water or water in oil emulsions since emulsions require shear in order to be formed while self-assembled structures don't.

The composition has a lipid continuous phase, or bulk lipid phase, rather than the lipid being dispersed in water as an emulsion. The lipid continuous phase is liquid at 25° C. A liquid is able to flow under gravity to take the shape of a container it is placed in. For example the lipid continuous phase may have a dynamic viscosity of less than 1 Pa·s at 25° C., for further example the lipid continuous phase may have a dynamic viscosity less than 0.5 Pa·s at 25° C., for further example less than 0.3 Pa·s at 25° C. The term oil refers to a liquid lipidic material, for example liquid at 25° C.

The phospholipids in the composition of the invention may be derived from a vegetable source, such as soy, canola, rapeseed, sunflower, wheat, or oat; or an animal source such as egg. Phospholipids derived from soy and canola are commercially available, e.g. as soy lecithin and canola lecithin. The phospholipid of the composition of the invention may be phosphatidylcholine, a component, for example, of lecithin. In order to form self-assembled structures in the oil phase, the phospholipid concentration in the oil phase must be larger than the CMC (critical micellar concentration) in the corresponding oil. Below this concentration, no self-assembled structures are formed. The phospholipids may be present in the composition at a level of at least 0.01 wt. %, for example at least 0.1 wt. %, for example at least 1 wt. %, for further example at least 2 wt. %. At lower levels of phospholipid the composition has lower viscosity. The skilled person will be able to adjust the phospholipid content to achieve the desired viscosity based on the desired application and the other components. The phospholipids may be present in the composition at a level between 0.01 wt. % and 40 wt. %, for example between 0.1 wt. % and 30 wt. %. Below 30 wt. % of phospholipid the self-assembled structures will always be liquid at 25° C. The water may be present in the composition at a level of at least 1 wt. %, for example at least 2 wt. %, for further example at least 5 wt. %. The amount of water should be chosen so as to ensure that the composition has a lipid continuous phase. For example, the composition of the invention may comprise between 1 and 50% water. The caffeine may be present in the composition at a level of at least 0.1 wt. %, for example at least 0.2 wt. %, for further example at least 0.5 wt. %.

The weight of oil in the composition of the invention may be greater than 1% of the total weight of oil and phospholipids, for example greater than 15% of the total weight of oil and phospholipids, for further example greater than 25% of the total weight of oil and phospholipids. Caffeine release is delayed during diffusion through the oil phase, so increasing the quantity of oil may further limit the rate of diffusion from the composition of the invention. It may be desirable to have higher quantities of oil since pure phospholipid has a strong taste which is moderated by the oil. The weight of oil in the composition of the invention may be between 1 and 99% of the total weight of oil and phospholipids, for example between 25 and 80% of the total weight of oil and phospholipids. The composition may be produced for example by homogenizing an oil with phospholipids, adding an aqueous solution of caffeine and mixing the resulting composition.

The oil comprised within the composition of the invention may comprise an essential oil. Essential oils are concentrated hydrophobic liquids obtained from plant materials. The essential oil may be the oil from a plant material selected from the group consisting of oregano, garlic, ginger, rose, mustard, cinnamon, rosemary, orange, grapefruit, lime, lemon, lemongrass, clove, clove leaf, vanilla, vanillin, mint, tea tree, thyme, grape seed, cilantro, lime, coriander, sage, eucalyptus, lavender, olive, olive leaf, anise, basil, pimento, dill, geranium, eucalyptus, aniseed, camphor, pine bark, onion, green tea, orange, artemisia herba-alba, aneth, citrus, marjoram, sage, ocimum gratissimum, *Thymus vulgaris*, cymbopogon citratus, *Zingiber officinale*, monodora myristica, *Curcuma longa*, coffee beans and a combination of these. Essential oils have good acceptance with consumers for example due to their widespread use in aromatherapy.

The oil comprised within the composition of the invention may be an essential oil. Common components of essential oils are terpenes. Lemon peel essential oil for example contains around 65% of the terpene limonene [V. I. Njoku et al., International Journal of Applied Sciences and Engineering Research, 3(2), 279-531 (2014)] The oil comprised within the composition of the invention may comprise terpenes, for example limonene, eucalyptol or diterpenes (including diterpene esters). The essential oil comprised within the composition of the invention may be selected from the group consisting of orange oil, lemon oil, mint (mentha arvensis) oil, spearmint oil, peppermint oil, coffee oil, eucalyptus oil and combinations of these. All of these essential oils comprise terpenes. The oil comprised within the composition of the invention may comprise limonene, for example, the oil comprised within the composition of the invention may be limonene. The oil comprised within the composition of the invention may comprise a mixture of terpenes with triglycerides, for example the oil comprised within the composition of the invention may comprise limonene and triglycerides, for further example the oil comprised within the composition of the invention may be an oil extracted from coffee beans, the oil comprising terpenes and triglycerides.

The self-assembled structures comprised within the composition of the invention may be selected from the group consisting of reversed L2 phase, reversed microemulsion (e.g. reversed L2 phase), reversed micellar cubic structure, reversed bicontinuous cubic structure, reversed sponge phase, reversed hexagonal structure, lamellar phase, inverse lamellar liquid crystalline phase and combinations of these. Reversed L2 phase, reversed microemulsion, reversed L2 phase, reversed micellar cubic structure, reversed bicontinuous cubic structure, reversed hexagonal structure and lamellar liquid crystalline phase are well known types of structures, for example as defined in Leser et al, 2006 (Advances in Colloid and Interface Science 123-126 (2006) 125-136). A reversed sponge phase is a disordered reversed bicontinuous cubic phase. An inverse lamellar liquid crystalline phase has some similarities with a standard lamellar liquid crystalline phase. However, in standard lamellar liquid crystalline phase, in the double layer the lipophilic tails are in contact with each other and the double layers are separated by a water layer while in an inverse lamellar liquid crystalline phase, the polar head are in contact with each other and the double layers are separated by a layer of oil. An inverse lamellar liquid crystalline phase may contain less than 10% water (for example less than 3%, for example less than 1%) and may contain more than 10% oil (for example more than 80%).

The self-assembled structures may be reversed micro emulsions, reversed micellar cubic structure, inverse lamellar phase or may be composed of reversed micelles. The self-assembled structures may be reversed micro emulsions or composed of reversed micelles. These structures enclose small aqueous domains and lipophilic domains which are particularly effective at limiting the diffusion of caffeine. The presence of self-assembled structures and their nature can be determined by the use of small angle X-ray scattering.

The composition of the invention may be for use in the treatment or prevention of drowsiness or impaired alertness. Caffeine is a central nervous system stimulant. Caffeine is known to have beneficial effects on both simple and complex attention tasks [Einöther, S. J. L. et al., Psychopharmacology, 225(2), 251-274. (2013)]. The composition of the invention provides the additional benefit of delivering the caffeine over a sustained time period. The composition of the invention may be combined with other medications, for example caffeine may be used in combination with ergotamine (for treatment of migraine and cluster headaches) or with certain pain relievers such as aspirin or paracetamol. When used in this way, caffeine may increase the effectiveness of the other medications. The composition of the invention may be combined with an antihistamine to overcome the drowsiness caused by the antihistamine.

The composition of the invention may be for use in the treatment or prevention of drowsiness or impaired alertness in an elderly subject. Alertness levels in the elderly are known to gradually decrease with age, affecting memory, reaction time and the ability to perform everyday tasks without making errors. Impaired alertness is a problem for not just elderly humans, but also for elderly pet animals. The composition of the invention may be for use in the treatment or prevention of drowsiness or impaired alertness in an elderly subject who is a human or a pet animal. A subject is considered as "elderly" if they have surpassed the first two thirds of their average expected lifespan in their country of origin, preferably if they have surpassed the first three quarters of the average expected lifespan in their country of origin, more preferably if they have surpassed the first four fifths of the average expected lifespan in their country of origin. For example, a human male born in the UK in 2010 has a life expectancy at birth of 78 years according to the UK Office of National Statistics, therefore they would be considered elderly at ages over 52 years, preferably over 58 years 6 months and more preferably over 62 years 5 months. For pets and livestock the species and breed should be taken into account. For example a Yorkshire Terrier dog has a life expectancy of about 12 years [E. J. Taylor et al., Proceedings of the Nutrition Society, 54, 645-656 (1995)] and so would be considered elderly at ages over 8 years, preferably over 9 years and more preferably over 9 years 7 months.

The composition of the invention may be for use in the treatment or prevention of obesity or being overweight. Caffeine has been shown to stimulate the metabolic rate in obese individuals [Acheson K J et al., Am J Clin Nutr. 33(5), 989-97 (1980)]. The composition of the invention provides the additional benefit of delivering the caffeine over a sustained time period.

The composition for use according to the invention may be administered in a daily dose to provide between 0.5 mg and 10 mg caffeine per 1 kg body weight. A typical cup of coffee provides around 75 mg of caffeine which, for a 60 kg subject is 1.25 mg per kg of body weight. The delayed release provided by the composition of the invention can therefore provide, over an extended period during the day, the equivalent of between less than one cup of coffee and up to 8 cups of coffee.

In a further aspect, the composition of the invention may be used non-therapeutically to improve attention and increase mental alertness. Many healthy individuals wish to increase their alertness, for example students studying late at night. It is therefore advantageous that the composition of the invention can provide a gradual release of caffeine to improve attention and increase mental alertness for healthy individuals over an extended period. Increased mental alertness may be manifested by increased mental sharpness, with increased speed of perception, comprehension or response.

The composition of the invention may further be used non-therapeutically to increase diet-induced thermogenesis and energy expenditure. Caffeine is known to increase thermogenesis and daily energy expenditure in lean humans [Dulloo A.G. et al., Am. J. Clin. Nutr., 49, 44-50. (1989)].

Healthy individuals who wish to control their body weight can therefore advantageously use the composition of the invention.

A further aspect of the invention is the use of the composition of the invention to provide a controlled release of caffeine. The slow diffusion of caffeine out of the composition provides a controlled release, for example, the caffeine may be released over a period of up to 12 hours, for example over a period of up to 6 hours, for further example over a period of up to 4 hours. The time of release will depend on the geometry of the edible composition and the total distance that the caffeine has to diffuse through the oil component. The caffeine may be released over a period of greater than 2 hours.

A still further aspect of the invention is an edible capsule comprising the composition of the invention, for example an edible capsule containing the composition of the invention. In the present invention the term capsule refers a relatively stable shell or membrane protecting its contents from the surrounding environment. Providing the composition of the invention in a capsule allows it to be, for example, taken orally or used as a suppository. The capsules may be soft-shelled capsules. The edible capsule may be a nutritional supplement.

Those skilled in the art will understand that they can freely combine all features of the present invention disclosed herein. In particular, features described for different embodiments of the present invention may be combined. Where known equivalents exist to specific features, such equivalents are incorporated as if specifically referred to in this specification. Further advantages and features of the present invention are apparent from the figure and non-limiting example.

EXAMPLES

Example 1: Caffeine Release from Phosphatidylcholine-Limonene System

Soybean phosphatidylcholine (PC) was purchased from Cargill, Germany, under the product name Epikuron 200. (R)-(+)-limonene and caffeine were purchased from Sigma-Aldrich. Mesophases (0.3 g) were prepared in Pyrex tubes with the following composition:

| Sample | $\alpha_{oil}$ | Water content (wt. %) |
|---|---|---|
| A | 36 | 28 |
| B | 55 | 35 |

Where $\alpha_{oil}$ is the ratio of phospholipid to the total weight of oil and phospholipids expressed as a percentage. Caffeine was dissolved in MilliQ water at 1% to form an aqueous phase. The PC and limonene were weighed into the tube and the mixture homogenized by vortexing. After a few hours equilibration, the aqueous phase was added and the tube was vortexed. After 2 days equilibration, the tubes were centrifuged at 3000 rpm for 5 minutes to obtain a flat surface. The tubes were kept in the dark.

Release studies were performed at room temperature in triplicates with an additional blank (non-loaded) sample. MilliQ water was used as a receiving solution. At the initial time, the tube was briefly rinsed with 2.7 g of the receiving solution. The tubes were then filled with 2.7 g of receiving solution. The receiving solution was fully exchanged at given times to create sink conditions. SAXS patterns were recorded before and after the release. SAXS patterns can slightly change during release experiments due to water absorption by the self-assembled structures and reduction of caffeine content due to diffusion of this compound to the aqueous matrix. Caffeine was detected in a quartz cuvette by UV-visible spectrometry at its absorption maxima of 273 nm, including background subtraction derived from the signal of the blank sample taken at the absorption maximum and at 600 nm, where caffeine does not absorb light. Averages and standard deviations (error bars) were calculated from cumulated release at each point.

The diffusion coefficients D were determined from the slope s of the linear fit in the initial release profile (below 30% release) as a function of the square root of time, using the Higuchi equation:

$$\frac{Q}{C_0} = 2\sqrt{\frac{D}{\pi}}\sqrt{t}$$

where Q is the molar flux of the drug through the surface S of the mesophase (S≈0.9 cm$^2$), $C_0$ is the initial molar concentration of caffeine in the mesophase, and t is the release time. Error bars on diffusion coefficients were calculated by the error propagation method for non-linear equations:

$$\frac{\Delta D}{D} = 2\frac{\Delta s}{s}$$

where $\Delta D$ and $\Delta s$ are the standard deviations of the diffusion coefficient and slope s.

Laboratory SAXS measurements were performed with a MicroMax-002+ microfocused X-ray machine (Rigaku), operating at 4 kW, 45 kV and 0.88 mA. The $K_\alpha$ X-ray radiation of wavelength $\lambda$=1.5418 Å emitted at the Cu anode is collimated through three pinholes of respective sizes 0.4, 0.3, and 0.8 mm. The scattered intensity was collected on a two dimensional Triton-200 X-ray detector (20 cm diameter, 200 μm resolution) normally for at least 30 minutes. The scattering wave vector is defined as q=4π sin(θ)/λ, where 2θ is the scattering angle. The SAXS machine is equipped with two sample chambers with different sample-to-detector distances, giving access to q ranges of 0.005 to 0.22 Å$^{-1}$ and 0.01 to 0.44 Å$^{-1}$ respectively. Silver behenate was used for q vector calibration. Scattered intensity data were azimuthally averaged using SAXS gui software (Rigaku). Samples were loaded in a Linkam hot stage with temperature control in a cell formed by two thin mica sheets and a rubber o-ring 1 mm-spacer.

The phase symmetry and lattice parameters were measured before and after the release experiments. Table 1 gives all parameters. The water domain dimensions were calculated according to Martiel [Martiel I. et al., Langmuir, 29(51.), 15805-12 (2013)] and Mezzenga [Mezzenga R. et al., Langmuir, 21, 3322-33. (2005)]. No phase change occurred in presence of caffeine, or at the end of the release experiment. Only a very limited swelling was observed (less than 10% change in lattice parameter). Caffeine has a significantly smaller size than the water domain dimensions, so that diffusion properties should not depend on the water domain dimensions but by the large distances of lipid domains to be crossed.

TABLE 1

Compositions and parameters of the mesophases of dimensionality d prepared for the release studies, just below the excess water limit.

| Sample | Phase (d) | Lattice param. (nm) | Polar domain radius (nm) | Lipid chain length (nm) |
|---|---|---|---|---|
| A | Reversed hexagonal (1) | 8.1 | 2.2 | 1.9 |
| B | Reversed micellar cubic (0) | 19.4 | 5.2 | 1.5 |

FIG. 1 shows the release curve of caffeine in sample B compared to release from pure water. The curve from sample A was essentially the same (the curves superimpose). The initial release profile could be fitted to the Higuchi equation. Diffusion coefficients ($cm^2/s$) are given in Table 2 below.

| Sample | Diffusion coefficient |
|---|---|
| A | 7.29E−07 |
| B | 6.68E−07 |
| Pure water | 6.30E−06 |

It can be seen that samples A and B (limonene/phospholipid with a lipid continuous phase and self-assembled structures) resulted in a diffusion coefficient for caffeine which was an order of magnitude lower than in pure water.

Example 2: Caffeine Release from Phosphatidylcholine-Limonene Liquid Systems with the Addition of Different Percentage of Coffee Oil Soybean phosphatidylcholine (Epikuron 200), (R)-(+)-limonene and caffeine were employed as in Example 1, while different percentages of coffee oil were added in the following experiments.

Mesophases (0.3 g) were prepared in Pyrex tubes with the following composition:

| Sample | $\alpha_{PC}$ | $\alpha_{CO}$ | Water content (wt. %) |
|---|---|---|---|
| C | 30 | 0 | 10 |
| D | 15 | 0 | 5 |
| E | 10 | 0 | 5 |
| F | 15 | 10 | 5 |
| G | 10 | 50 | 5 |

Where $\alpha_{PC}$ is the ratio of phospholipid and $\alpha_{CO}$ is the ratio of coffee oil to the total weight of oil, phospholipids and coffee oil respectively, expressed as a percentage.

Sample preparation, release studies, caffeine detection and SAXS measurements were performed in the same manner as in Example 1. In this case, being the mesophase liquid, the release studies were performed slightly differently because the oil phase was on the top of the water phase. The water phase, which is the release receiving solution, was extracted each time by means of a syringe and exchanged accordingly at given times to create sink conditions. The diffusion coefficients ($cm^2/s$) were calculated in the same way as in Example 1 and they are given in Table 3 below.

| Sample | Diffusion coefficient |
|---|---|
| C | 1.49E−06 |
| D | 4.79E−06 |
| E | 4.79E−06 |
| F | 2.24E−06 |
| G | 2-29E−06 |
| Pure water | 6.30E−06 |

It can be seen that also in the liquid form, the system preserve a sustained release behavior. In fact the diffusion coefficients obtained for caffeine are lower than in pure water.

Figure 2:
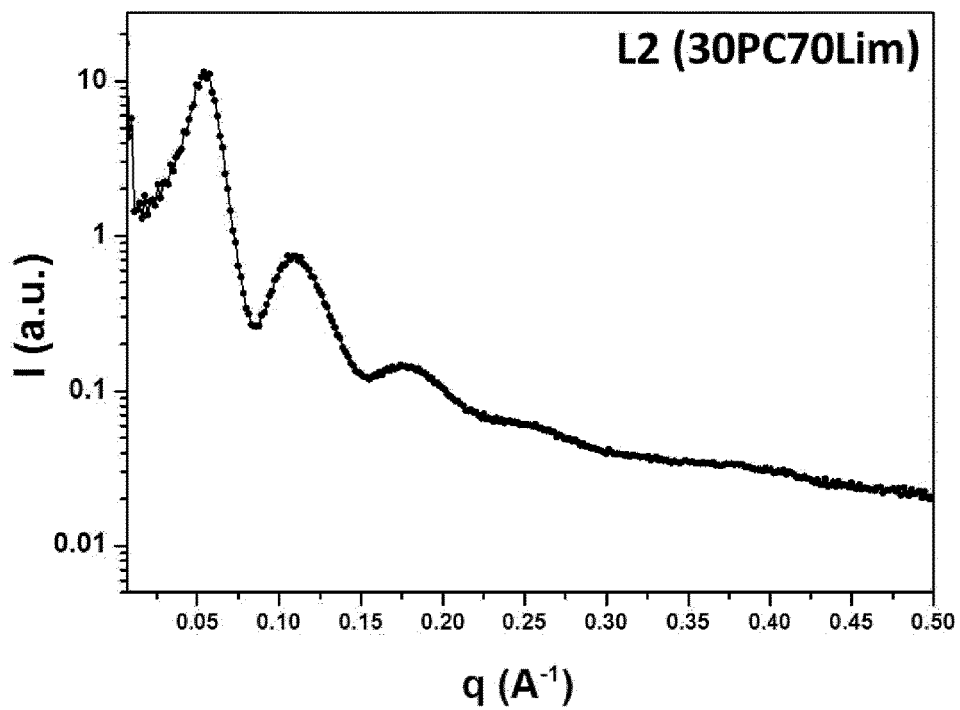
FIG. 2 shows the small angle X-ray scattering curves of a reverse microemulsion (L2) having the composition 30% PC 70% limonene and excess of aqueous phase containing caffeine.
Figure 3:
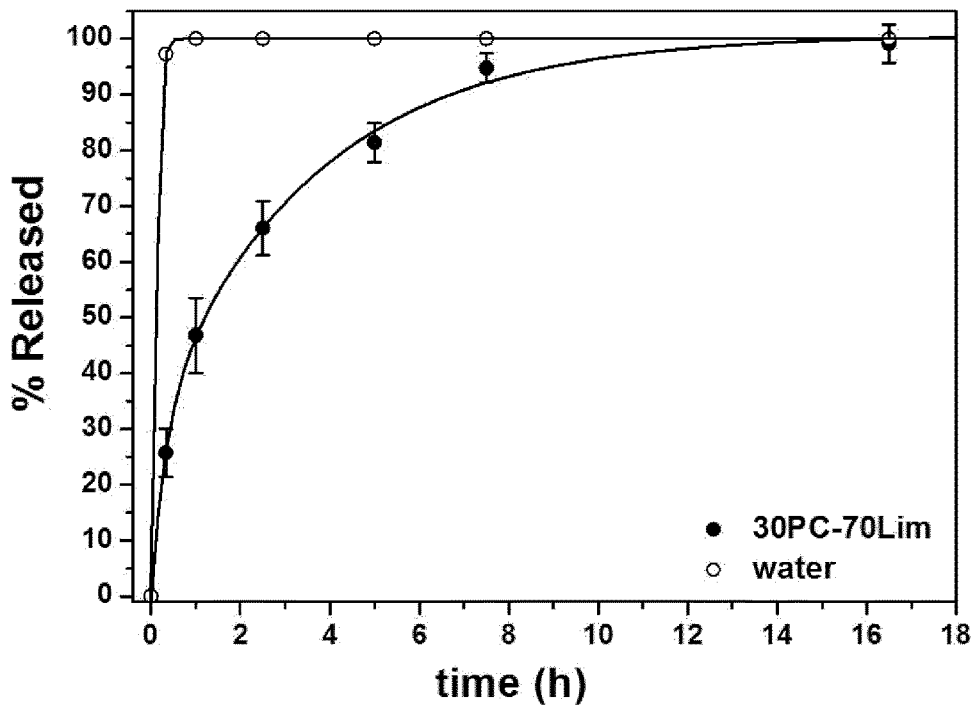
FIG. 3 shows the release curve corresponding to the reverse microemulsion of FIG. 2.

FIG. 2 shows the small angle X-ray scattering curves of a reverse microemulsion (L2) having the composition 30% PC 70% limonene and excess of aqueous phase containing caffeine. SAXS was taken at the end of the release experiment. The peaks or bumps indicate that a self-assembled structure is present. The corresponding phase (self-assembled structure) is an L2 (also called reversed microemulsion) phase. It is liquid at room temperature just after processing and after release took place. FIG. 3 shows the release curve corresponding to the reverse microemulsion of FIG. 2. Note that (diffusion) from this self-assembled structure (L2) is low compared to diffusion in water leading to sustained release from this reversed microemulsion.

Figure 4:
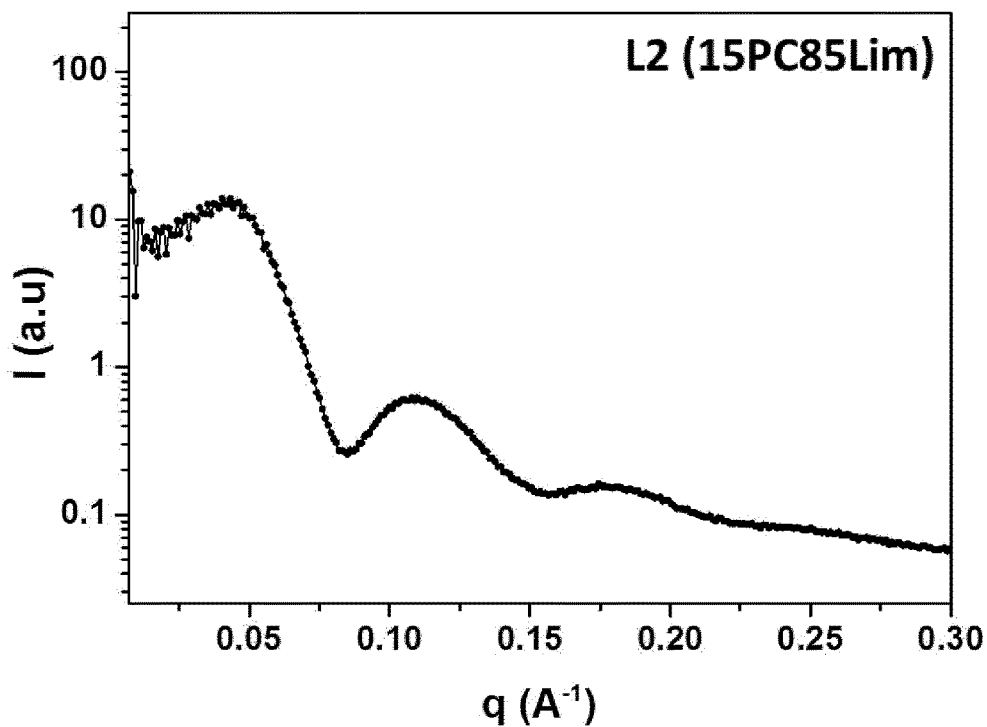
FIG. 4 shows the small angle X-ray scattering curves of a reverse microemulsion (L2) having the composition 15% PC 85% limonene and excess of aqueous phase containing caffeine.
Figure 5:
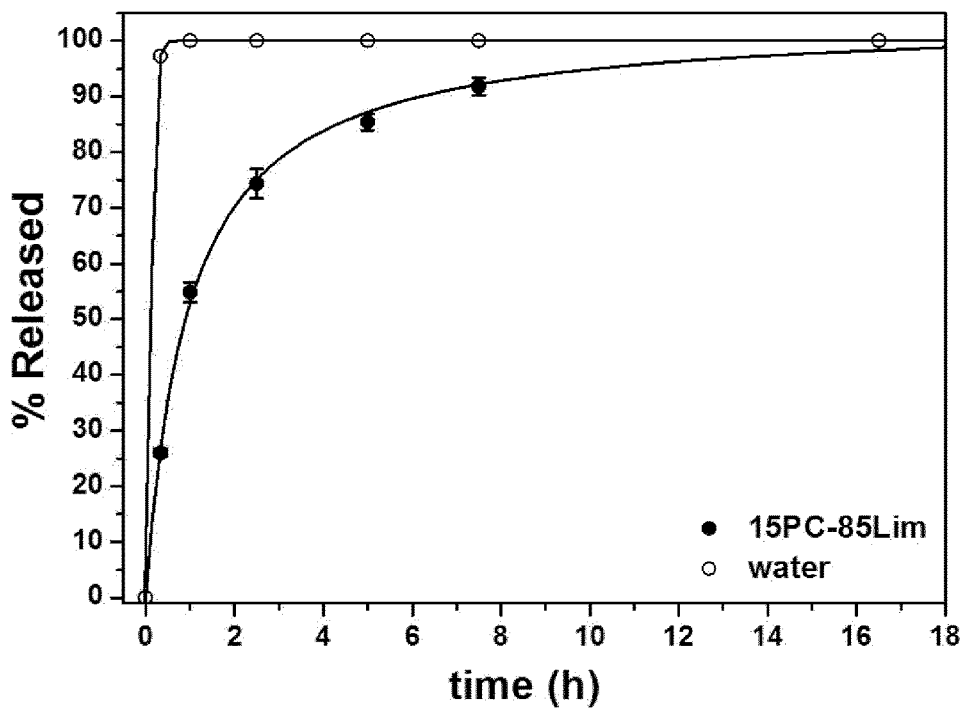
FIG. 5 shows the release curve corresponding to the reverse microemulsion of FIG. 4.

FIG. 4 shows the small angle X-ray scattering curves of a reverse microemulsion (L2) having the composition 15% PC 85% limonene and excess of aqueous phase containing caffeine. The peaks or bumps indicate that a self-assembled structure is present. The corresponding phase (self-assembled structure) is an L2 also called reversed microemulsion phase. It is liquid at room temperature just after processing and after release took place FIG. 5 shows the release curve corresponding to the reverse microemulsion of FIG. 4. Note that diffusion from this self-assembled structure (L2) is low compared to diffusion in water leading to sustained release from this reversed microemulsion.

Figure 6:
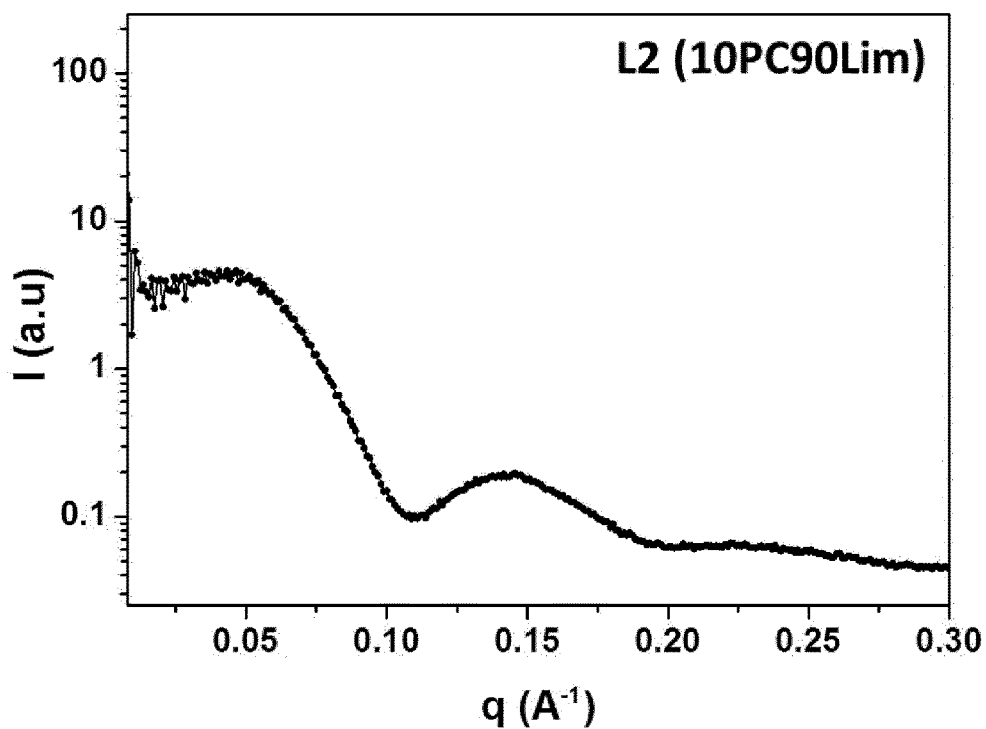
FIG. 6 shows the small angle X-ray scattering curves of a reverse microemulsion (L2) having the composition 10% PC 90% limonene excess of aqueous phase containing caffeine.
Figure 7:
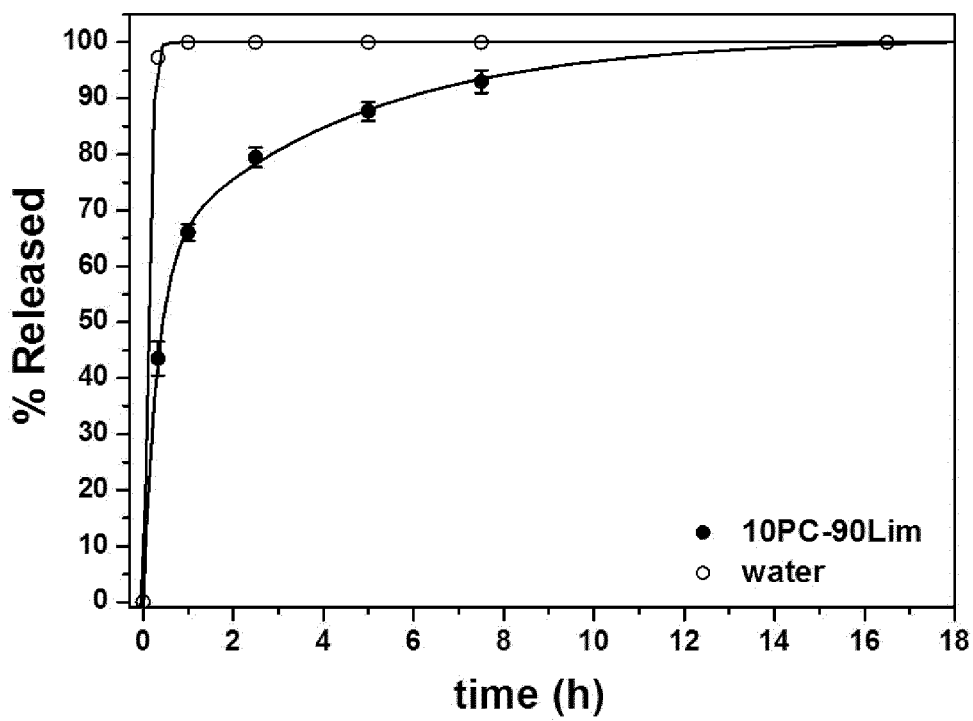
FIG. 7 shows the release curve corresponding to the reverse microemulsion of FIG. 6.

FIG. 6 shows the small angle X-ray scattering curves of a reverse microemulsion (L2) having the composition 10% PC 90% limonene excess of aqueous phase containing caffeine. The peaks or bumps indicate that a self-assembled structure is present. The corresponding phase (self-assembled structure) is an L2 also called reversed microemulsion phase. It is liquid at room temperature just after processing and after release took place FIG. 7 shows the release curve corresponding to the reverse microemulsion of FIG. 6. Note that (diffusion) from this self-assembled structure (L2) is low compared to diffusion in water leading to sustained release from this reversed microemulsion.

Figure 8:
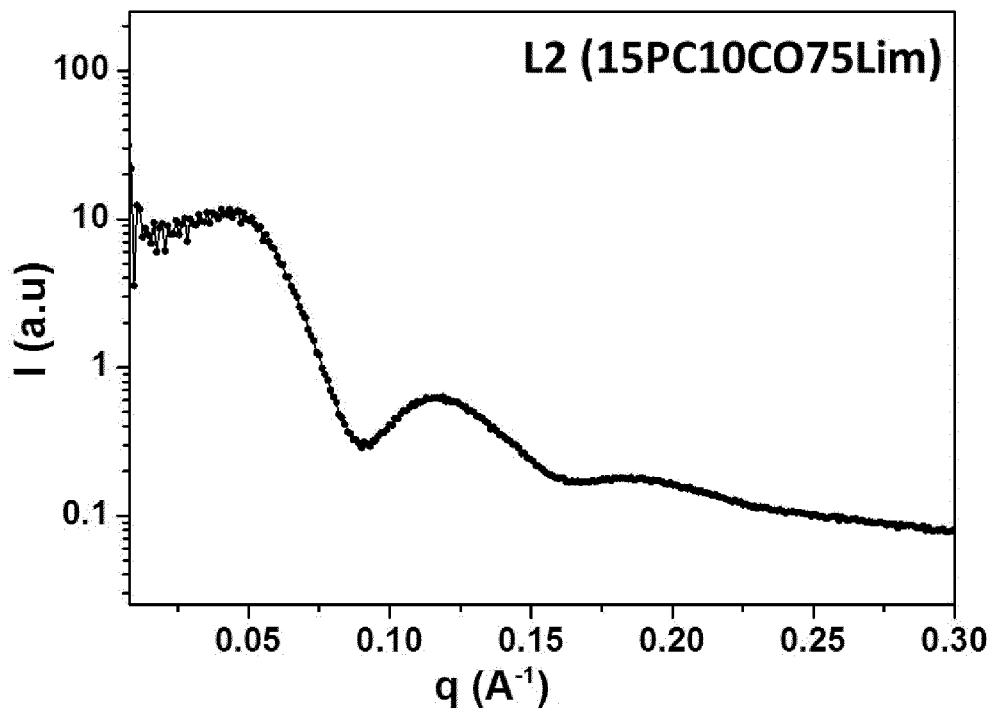
FIG. 8 shows the small angle X-ray scattering curves of a reverse microemulsion (L2) having the composition 15% PC 75% limonene 10% coffee and excess of aqueous phase containing caffeine.
Figure 9:
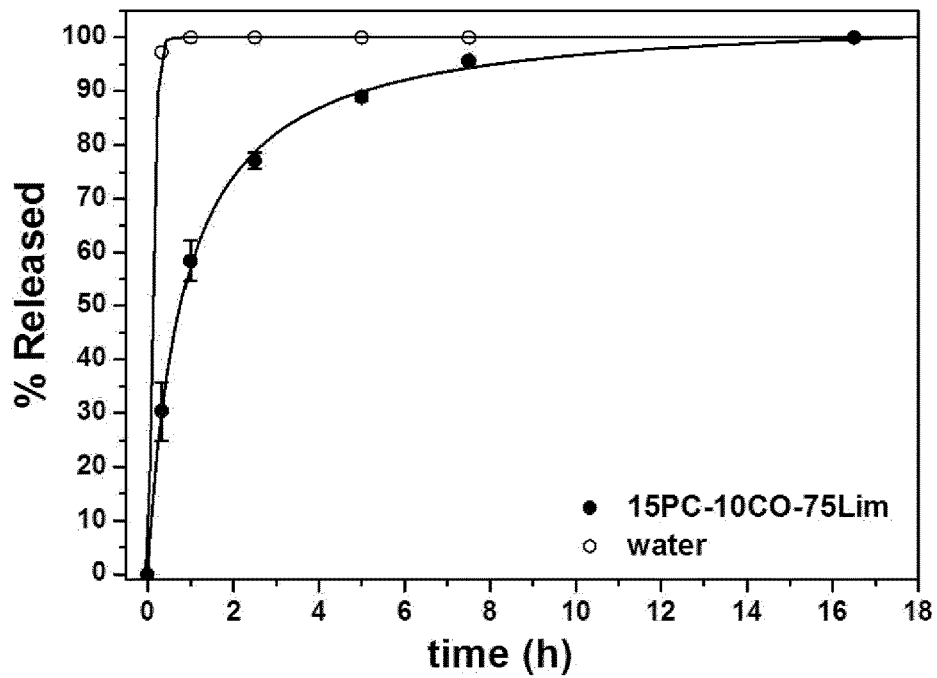
FIG. 9 shows the release curve corresponding to the reverse microemulsion of FIG. 8.

FIG. 8 shows the small angle X-ray scattering curves of a reverse microemulsion (L2) having the composition 15% PC 75% limonene 10% coffee and excess of aqueous phase containing caffeine. The peaks or bumps indicate that a self-assembled structure is present. The corresponding phase (self-assembled structure) is an L2 also called reversed microemulsion phase. It is liquid at room temperature just after processing and after release took place FIG. 9 shows the release curve corresponding to the reverse microemulsion of FIG. 8. Note that (diffusion) from this self-assembled structure (L2) is low compared to diffusion in water leading to sustained release from this reversed microemulsion.

Figure 10:
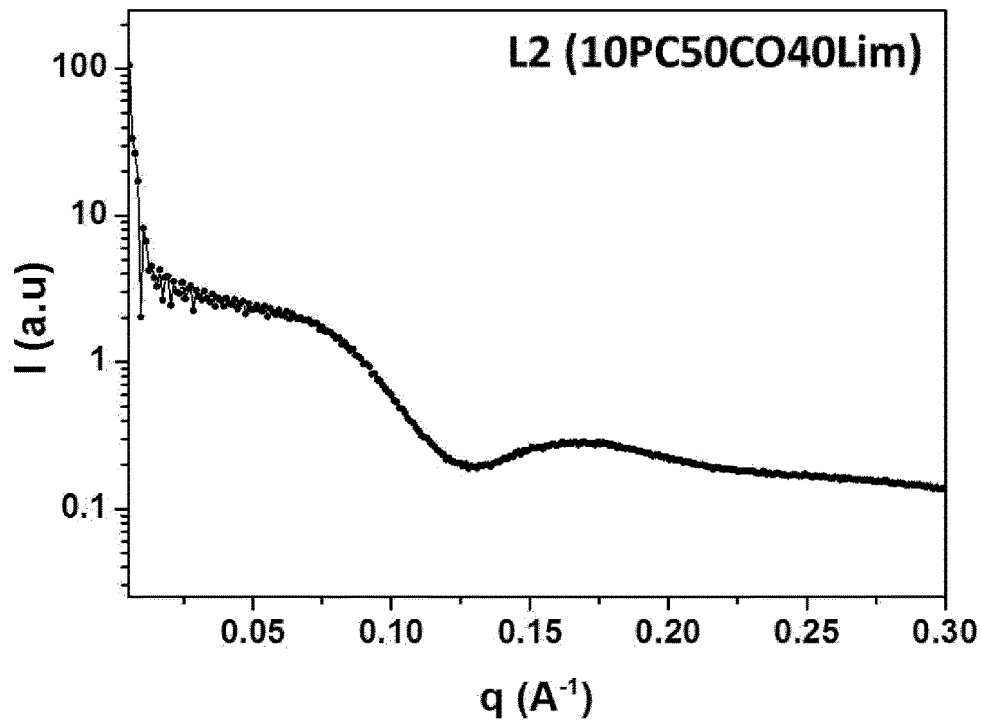
FIG. 10 shows the small angle X-ray scattering curves of a reverse microemulsion (L2) having the composition 10% PC 40% limonene 50% coffee oil and an excess of aqueous phase containing caffeine.
Figure 11:
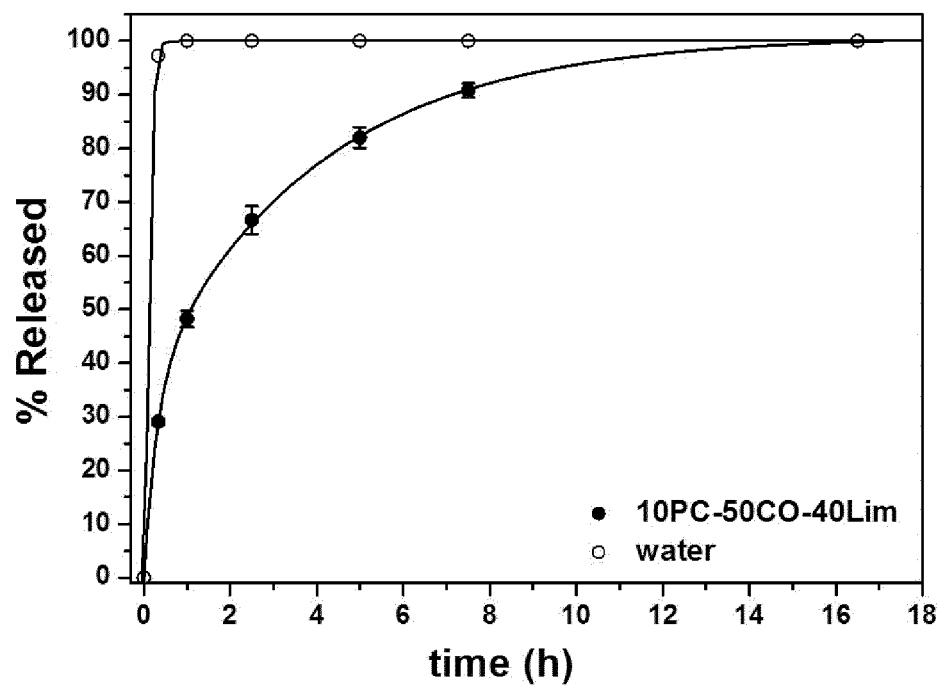
FIG. 11 shows the release curve corresponding to the reverse microemulsion of FIG. 10.

FIG. 10 shows the small angle X-ray scattering curves of a reverse microemulsion (L2) having the composition 10% PC 40% limonene 50% coffee oil and excess of aqueous phase containing caffeine. The peaks or bumps indicate that a self-assembled structure is present. The corresponding phase (self-assembled structure) is an L2 also called reversed microemulsion phase. It is liquid at room temperature just after processing and after release took place. FIG. 11 shows the release curve corresponding to the reverse microemulsion of FIG. 10. Note that diffusion from this self-assembled structure (L2) is low compared to diffusion in water leading to sustained release from this reversed microemulsion.

The invention claimed is:

1. An edible composition consisting of oil, between 0.1 wt. % and 30 wt. % of phospholipids, at least 0.5 wt. % of caffeine, and between 5 and 50% wt. % of water, the oil being between 25 and 80% of the total weight of the oil and the phospholipids, the oil comprises coffee oil, and the caffeine is released from the edible composition over a time period of at least 4 hours, the edible composition forming a lipid continuous phase which is liquid at 25° C., and the edible composition also forming self-assembled structures selected from the group consisting of a reversed hexagonal structure, a reversed micellar cubic structure, and combinations thereof.

2. The edible composition according to claim 1, wherein the oil further comprises an additional essential oil selected from the group consisting of orange oil, lemon oil, mint oil, spearmint oil, peppermint oil, *eucalyptus* oil and combinations of these.

3. A method for treatment of drowsiness or impaired alertness, the method comprising administering to a subject in need thereof a composition consisting of oil, between 0.1 wt. % and 30 wt. % of phospholipids, at least 0.5 wt. % of caffeine, and between 5 and 50% wt. % of water, the oil being between 25 and 80% of the total weight of the oil and the phospholipids, the oil comprises coffee oil, and the caffeine is released from the composition over a time period of at least 4 hours, the edible composition forming a lipid continuous phase which is liquid at 25° C., and the edible composition also forming self-assembled structures selected from the group consisting of a reversed hexagonal structure, a reversed micellar cubic structure, and combinations thereof.

4. The method according to claim 3, wherein the subject is elderly.

5. The method according to claim 3, wherein the subject is a human or a pet animal.

6. A method for treatment of obesity or being overweight, the method comprising administering to a subject in need of same a composition consisting of oil, between 0.1 wt. % and 30 wt. % of phospholipids, at least 0.5 wt. % of caffeine, and between 5 and 50% wt. % of water, the oil being between 25 and 80% of the total weight of the oil and the phospholipids, the oil comprises coffee oil, and the caffeine is released from the composition over a time period of at least 4 hours, the edible composition forming a lipid continuous phase which is liquid at 25° C., and the edible composition also forming self-assembled structures selected from the group consisting of a reversed hexagonal structure, a reversed micellar cubic structure, and combinations thereof.

7. The method according to claim 3, wherein the composition is administered in a daily dose to provide between 0.5 mg and 10 mg of the caffeine per 1 kg body weight of the subject.

8. The method of claim 3, wherein the composition is in an edible capsule.

9. The edible composition according to claim 1, wherein the composition is in an edible capsule.

10. The method according to claim 6, wherein the composition is administered in a daily dose to provide between 0.5 mg and 10 mg of the caffeine per 1 kg body weight of the subject.

11. The method of claim 6, wherein the composition is in an edible capsule.

12. The edible composition according to claim 1, wherein the phospholipids comprise phosphatidylcholine, and the oil further comprises limonene.

13. The edible composition according to claim 1, wherein the phospholipids are from 36 wt. % to 55 wt. % of the total weight of the oil and the phospholipids.

14. The edible composition according to claim 1, wherein the water is 28 wt. % to 35 wt. % of the edible composition.

15. The edible composition according to claim 1, wherein the oil further comprises limonene and a weight ratio of the phospholipids: the limonene: the coffee oil is from about 1:4:5 to about 3:15:2.

16. The method of claim 3, wherein the oil further comprises limonene and a weight ratio of the phospholipids: the limonene: the coffee oil is from about 1:4:5 to about 3:15:2.

17. The method of claim 6, wherein the oil further comprises limonene and a weight ratio of the phospholipids: the limonene: the coffee oil is from about 1:4:5 to about 3:15:2.

* * * * *